United States Patent [19]

Dieterich

[11] 4,244,359
[45] Jan. 13, 1981

[54] ORTHOPEDIC SANDAL

[76] Inventor: Alfred Dieterich, Westtorgraben 3, 8500 Nurnberg, Fed. Rep. of Germany

[21] Appl. No.: 78,715

[22] Filed: Sep. 25, 1979

[30] Foreign Application Priority Data

Sep. 30, 1978 [DE] Fed. Rep. of Germany ....... 2842815

[51] Int. Cl.³ ............................................. A61F 5/00
[52] U.S. Cl. .................................................. 128/81 R
[58] Field of Search .................. 128/81 R, 581, 583, 128/584, 585; 36/94, 7.5

[56] References Cited

U.S. PATENT DOCUMENTS

| 2,958,324 | 11/1960 | Berkemann | 128/81 R |
| 3,049,120 | 8/1962 | Marcus | 128/81 R |
| 3,066,678 | 12/1962 | Riecken | 128/81 R |
| 3,219,032 | 11/1965 | Levitt | 128/81 R |

Primary Examiner—John D. Yasko
Attorney, Agent, or Firm—Holman & Stern

[57] ABSTRACT

An orthopedic sandal for correction of hammer toes and Hallux Valgus (X-toe) being a lever arm extending along the longitudinal axis of the sole of a sandal and being pivotally connected to the sole in its rearward portion. A toe holding bar for pressing the toes downward is connected to the free end of the lever arm and various embodiments of mechanisms for moving the large toe medially for correcting Hallux Valgus are operatively associated with the lever arm. Further mechanisms for stretching the large toe in conjunction with the intermittent treatment of the Hallux Valgus are operatively interconnected with the mechanisms for moving the large toe medially.

22 Claims, 15 Drawing Figures

ORTHOPEDIC SANDAL

BACKGROUND OF THE INVENTION

The instant invention concerns an orthopedic sandal being provided with a lever arrangement for the corrective treatment of hammer toes.

A lever arrangement in a sandal sole is activated by placing the foot onto the sandal, and to thereby transmit a force on the toes which corrects the position of the hammer toes, and wherein preferably simultaneously a force is transmitted by means of the pressure of the foot intermittently affecting the large toe, forcing same inwardly (medially) for correcting the Hallux Valgus (so-called X-position of the toes). Hammer toes are defined to be partially-stiff toes where the basic joints of the toes are in an over-stretched position and the middle and end joints are in a bent position and are either partially or totally stiff. Previously, successful treatment of hammer toes was only possible by surgery. One type of sandal, however, is known in the art in which a thin aluminum plate is placed from the top onto the stretch-contraction of the toes. An elastic rubber-band is guided around this plate and below the bottom surface of the sandal and is stretched. The stress force of this rubber-band should stretch the hammer toes. However, when the pressure is heavy enough to effect the treatment, blood circulation is cut off. It is furthermore disadvantageous that at the moment of main stress on the front portion of the foot, i.e., during walking, the pressure of the device is released.

Hallus Valgus is a condition wherein the large toe of the foot is partially stiffened at its base joint, with a deviation of its position toward the outer side of the foot and in many instances may be pointed upwards to some extent. Corrective treatment procedures as known in the prior art exist only in the form of daily bandagings and by nightly applications of a splint, exclusively for the separate treatment of the Hallus Valgus. This condition appears, however, mostly in combination with hammer toes. Thus, a treatment for one condition is not necessarily suitable for the other.

Further, hammer toes and Hallus Valgus appear mostly in connection with a pronounced splay foot. A splay foot represents a deformation of the front portion of the foot whereby the transveral arch which is located somewhat behind the center metatarsal heads I-V no longer extend convexly upward, but run convexly downward, whereby the transverse diameter of the frontal portion of the foot is widened.

It is an object of the instant invention to provide for an improvement of the corrective effects of orthopedic sandals and in providing further advantageous embodiments for such a sandal, wherein necessarily also an intermittent correction of the hammer toe should be provided.

In order to solve the above-noted problem, the instant invention proposes mainly that the lever arrangement, or a device effecting said lever arrangement, be located at least in the rearward area of the sole of the sandal, and thus becomes activated primarily by means of a pressure of the rearward portion of the foot. It has been proven that for stretching, i.e., correction of the position of the hammer toes, it is better when thereby the foot not yet be raised, i.e., the basic joints of the toes are not overstretched. This effect of the instant invention is still further strengthened in that when a person is standing up, or walking, the pressure of the rearward portion of the foot, namely the heel, is relatively strong so that there develops in the whole a correspondingly strong stretching effect. Thus, it is during the beginning of the step that the load of the lever arrangement by the rearward area of the foot is strongest, in order that the stress be lesser during the final phase of the rolling-up of the foot when walking, i.e., in the second phase of the walking movement, until with the lifting off of the foot, the stress returns to zero.

A hammer toe formation appears often in connection with a splay foot. The instant invention therefore proposes further that a splay foot bandage encircling the foot be attached to the lever arrangement or device in such a manner so that with the intermittent pressure of the foot, the splay foot bandage presses the foot together in a proper corrective sense. This will produce on one hand, an intermittent and thereby especially effective correction of the splay foot; and on the other, the extreme correction of the hammer toe position results simultaneously in the spreading of the front portion of the foot, which, however, is prevented by the aforementioned characteristics of the present invention.

The instant invention proposes further that means for stretching the large toe are coupled with the intermittent correction of Hallux Valgus. This results in a stretching of the basic joint of this toe in order to improve the metabolism in the field of this joint. This stretching can be done together with the movement of the large toe to the medial.

It can be seen that a sandal made to the design of the present invention can be manufactured with very simple means and therefore at economical costs. Thus, the corrective treatment of hammer toes is thereby made simple and effective. There exists no danger of cutting off blood circulation in the foot. The present invention represents to the patient a substantial improvement with regard to time and money, since normally intermittent treatment of these conditions of the foot was possible only by means of physical therapy. The treatment costs necessary for physical therapy are many times higher than the purchasing price of a sandal in accordance with the present invention. It has been proven that it is difficult and very expensive for a patient to subject oneself regularly to a physical therapy treatment. In contrast therewith, the patient is able to wear the inventive sandal at any suitable occasion. The utilization of the inventive sandal has an influence on the front portion and the toes of the foot which counteracts the damaging effects caused by modern shoes which are pointed at the front and have heels which are excessively high.

BRIEF DESCRIPTION OF THE DRAWINGS

Further advantages and characteristics of the present invention are contained in the dependent claims, as well as in the following description of embodiments and the associated drawings, wherein:

DETAILED DESCRIPTION OF PREFERRED EMBODIMENTS

The embodiment of FIGS. 1 to 4 shows a possible embodiment of the pressure-transmission from the rearward portion of the foot, as well as also a splay foot correction, and a correction of the Hallux Valgus with a stretching of the large toe.

A lever arrangement is emplaced in the sole 1 of the sandal, for example in cavities 2 and 2' consisting of lever arm 4 extending in the longitudinal direction of the sole and being pivoted on the sole at pivot point 3, and an activating cross-lever arm 5 connected to lever arm 4 at a distance from the pivot point 3. A secondary sole 6 is arranged above this lever arrangement on to which the foot is placed. The secondary sole 6 is resilient and bendable in its frontal position only. The rearward, rigid portion of the secondary sole 6 is upwardly and downwardly movable with the movement of the foot. The toe-holding bar 7 is fastened to activating cross-lever arm 5 by fastening means which can be, for example, two pairs of screws 7'''. The screws penetrate the vertical slots of the inner extension 7' and the outer extension 7'' of the bar so that the bar 7 is adjustable to the lever arm arrangement upwardly as well as angularly.

A load receiving crossbar 8 is attached to the rearward portion of the rigid pressure or lever arm 4. The crossbar 8 is in direct physical contact with the secondary sole 6 located thereabove, and, by means of the stress of the heel pressure (see arrow A in FIG. 2) can be pushed downwards. When the sandal is also provided with a corrective possibility for the Hallux Valgus, a possibility for stretching the large toe, and a possibility for correcting the splay foot (in this regard, reference is made to the additional embodiment), then all corrective possibilities are made synchronously and intermittently, according to the respective stress exerted by means of the foot. The effective strength of the corrective movement, when required, may be altered by inserting the crossbar 8 into the various holes 9 of the lever arm 4, whereby the lever translation is changed. The crossbar 8 and the holes 9 are thereby located in the rearward portion of the sole of the sandal.

Figure 1:
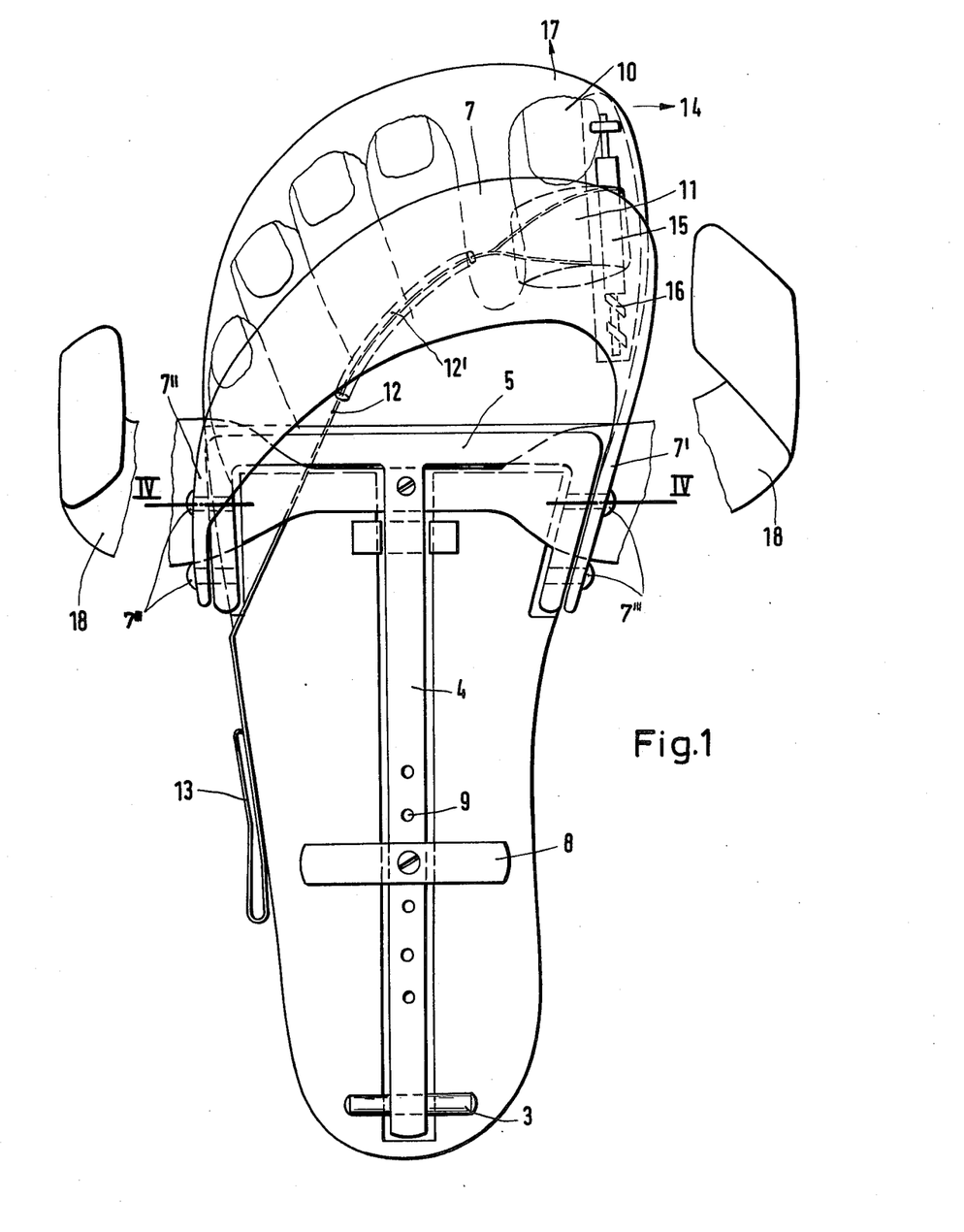
FIG. 1 shows a top plan view of the first embodiment with the large toe in a corrective position, whereby a plurality of corrective devices of the present invention are shown.
Figure 2:
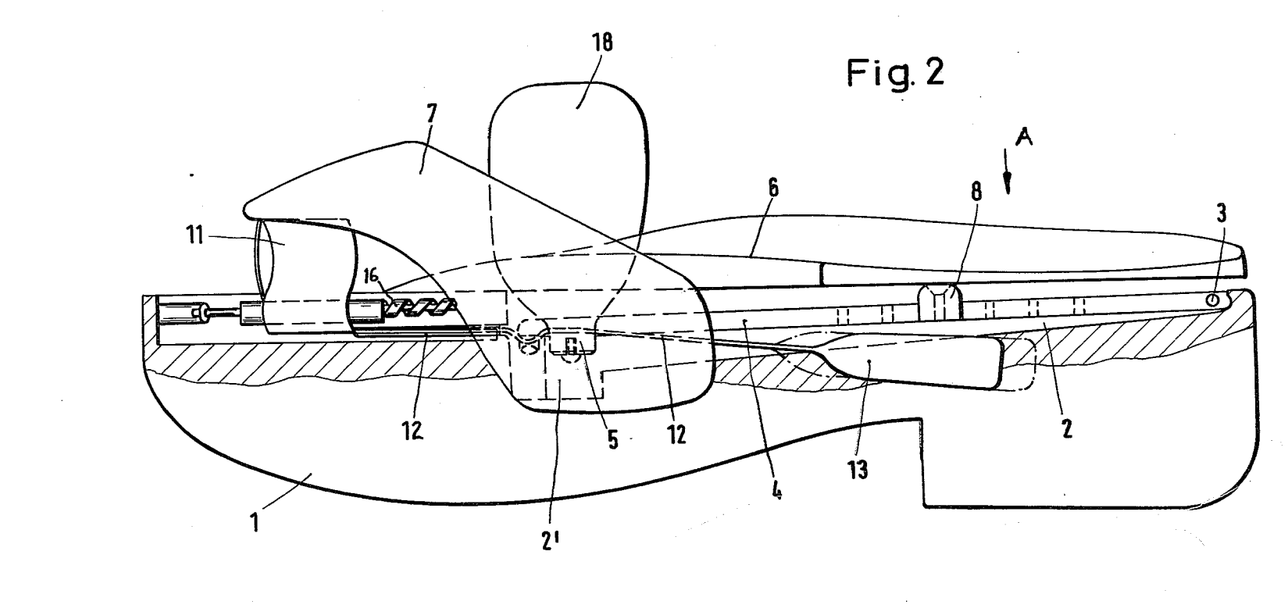
FIG. 2 represents an associated lateral view, partially in cross-section, whereby the parts are in a released position.
Figure 3:
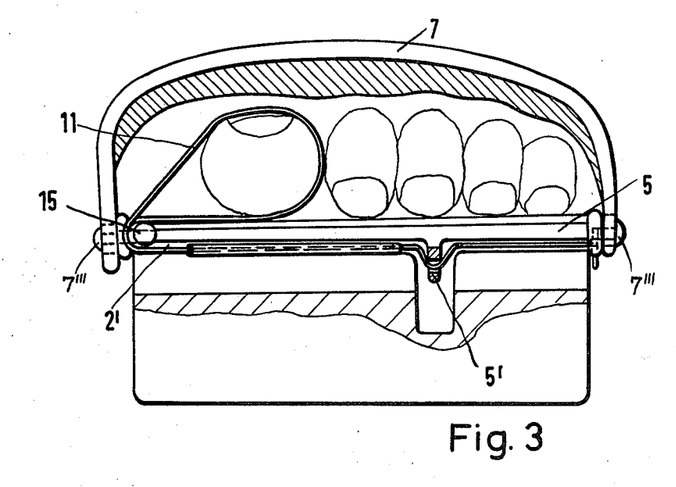
FIG. 3 is a front plan view of the frontal half portion of the sandal according to FIGS. 1 and 2 in a relaxed position, whereby the parts at an elevation are drawn on a somewhat increased scale, partially in cross-section.
Figure 4:
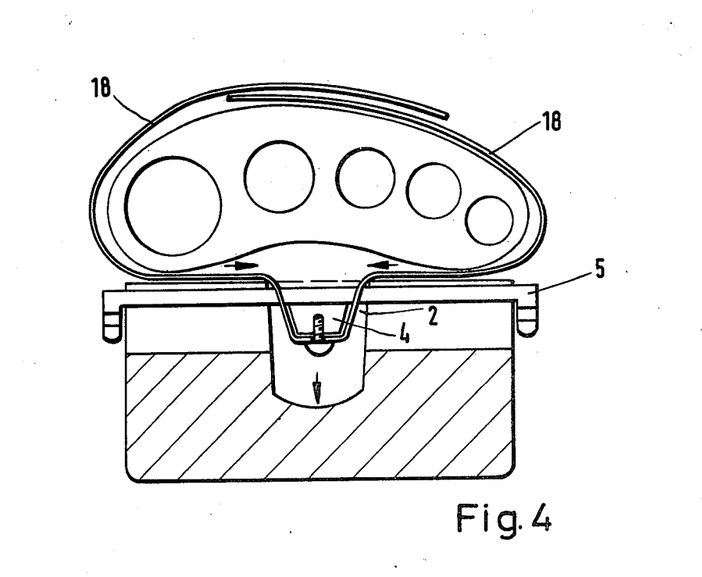
FIG. 4 represents a cross-sectional view according to lines IV—IV in FIG. 1, also in a relaxed position, i.e., in a non-stressed position.

The Hallux Valgus correction in this embodiment is made by means of a loop 11, which is guided between the large toe and the toe adjacent thereto and looped around the large toe (FIG. 3). The free end of the loop is fastened to a pull-tape or wire 12, the end 13 of which is adjustably fastened to the edge of the sole 1. The tape or wire 12 runs in a bowden cable-type control arrangement 12' in a cavity 2' of the sole 1 and is guided below the activating cross-lever arm 5 through a slot 5' located thereon (see also FIG. 3). When the activating cross-lever arm 5 is pushed downwards, the wire 12 is stretched and pulls the large toe 10 via the loop 11 to the medial (direction of the arrow 14). The above mentioned stretching of the pull wire 12 and therewith of the loop 11, may be varied by attaching the end 13 of the wire 12 at a different point of the edge of the sole 1.

The simultaneous stretching of the large toe in the base joint in this embodiment is effected by means of a roller around which is guided the loop 11 (see also FIG. 3). The roller means 15 is rotatably positioned on an outwardly spiral threaded positioning pin 16 in a corresponding spiral threading of the sole so that a rotating of roller 15 results in its displacement in its longitudinal direction. When the roller 15 is provided with a corresponding rough surface area, it will pick up the loop 11 and the large toe stretches in the direction of the arrow.

Two tapes 18 are fastened onto the activating lever arm 5, and their opposite ends may be secured together by a securing means (not shown). These form the bandage for the splay foot. As shown especially in FIG. 4, a downward pressing of the lever arrangement results in a movement of the tapes 18 by means of activating lever arm 4 in the directions of the arrow as shown and the thusly initiated relative reduction of its foot-section produces the splay-foot correction.

Figure 5:
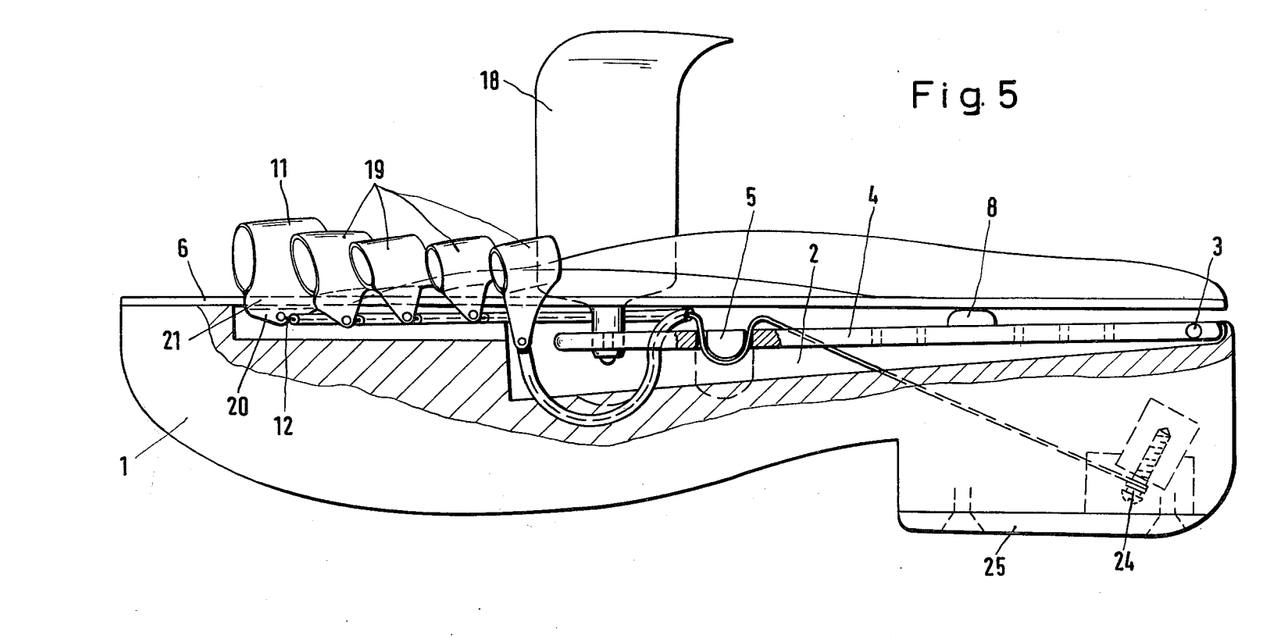
FIGS. 5 and 6 show a lateral view (partially in cross-section) and a top plan view of a further embodiment of the present invention, with a hammer toe correction by means of loops.
Figure 6:
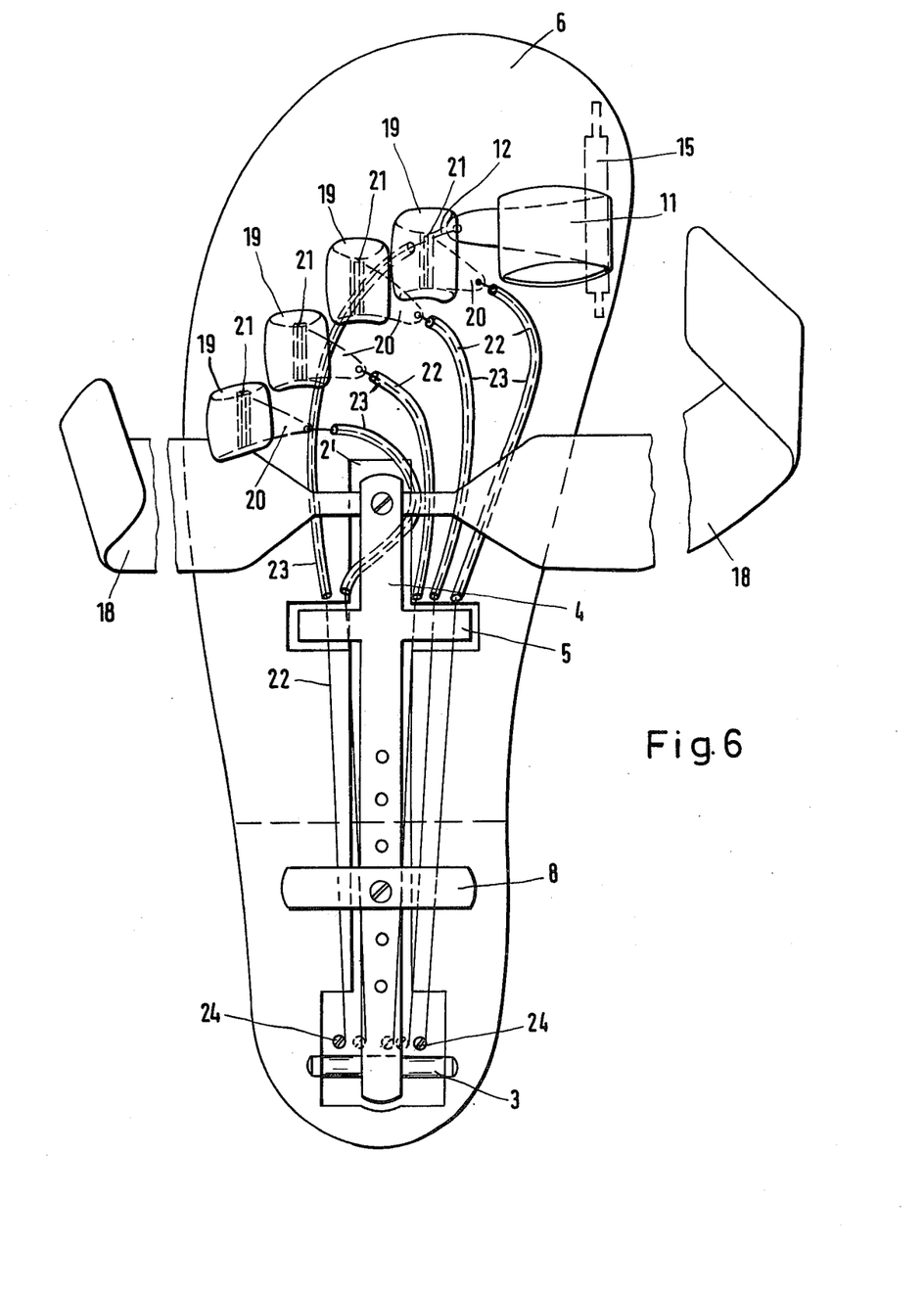

In the embodiment seen in FIGS. 5 and 6, the lever arrangement is basically constructed as in the embodiment of FIGS. 1 to 4, including the splay foot bandage 18. Identical reference numerals are used for basically identical parts. To correct the hammer toe position, secondary loops 19 are present for the second to the fifth toe. Tongues 20 are located on secondary loops 19 which are guided through the slots 21 of the secondary sole 6. Secondary pull wires 22 engage the tongues 20 and extend below the secondary sole 6 in a bowden cable-type control arrangement 23, thereby guiding the wires below the activating cross-lever arm 5. The opposite end of each wire is fastened to a tightening screw 24. The turning of each screw 24 winds the respective wire thereon (see especially FIG. 5). With the turning of each screw 24 (in this embodiment, after the lower heel-cover 25 is loosened) the stretching of each wire 22 is adjusted to the required initial value. The same structure can be used for the wire 12 of loop 11 which surrounds the large toe. It is seen that a downward pushing of the lever arm 4 via the activating cross-lever arm 5 results in an additional stressing of the wires. The toes two to five which are placed into secondary loops 19 are thereby moved downwards by the loops, i.e., the hammer toe position is being corrected. Simultaneously, the large toe is pulled towards the medial by loop 11.

The slots 21 in the secondary sole 6 prevent thereby a twisting of the toe loops. The tongues 20 after penetrating the slots 21, can be bent away laterally, thereby preventing the secondary loops 19 from being pulled out of the slots 21. The bowden cable-type control arrangement may be fused into the material of the sole 1.

Figure 7:
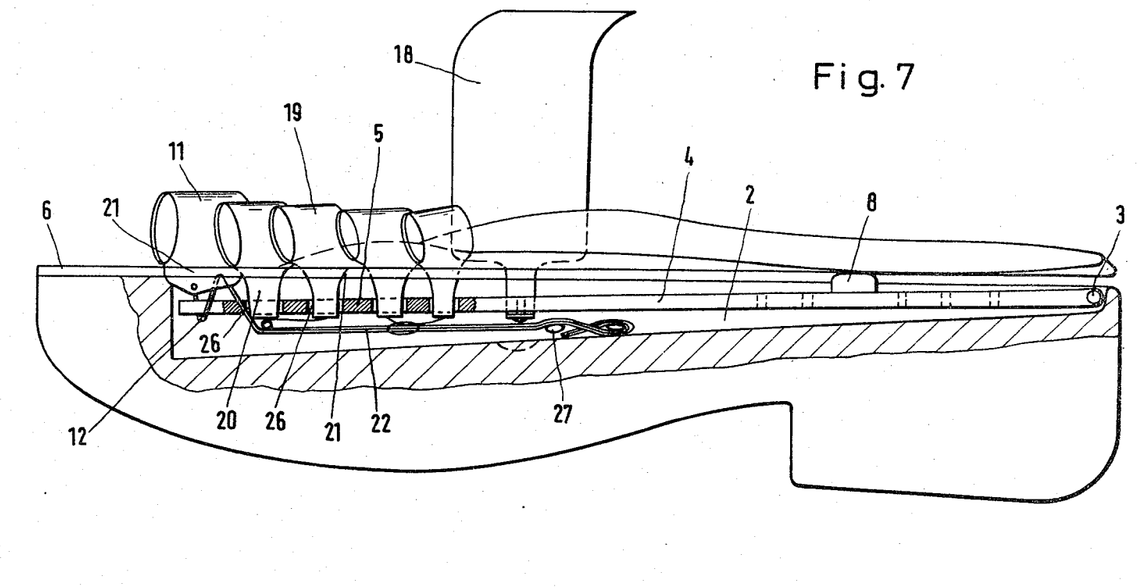
FIGS. 7 and 8 also show a lateral view (partially in cross-section) and a top plan view of a further embodiment of the present invention with a hammer toe correction by means of loops.
Figure 8:
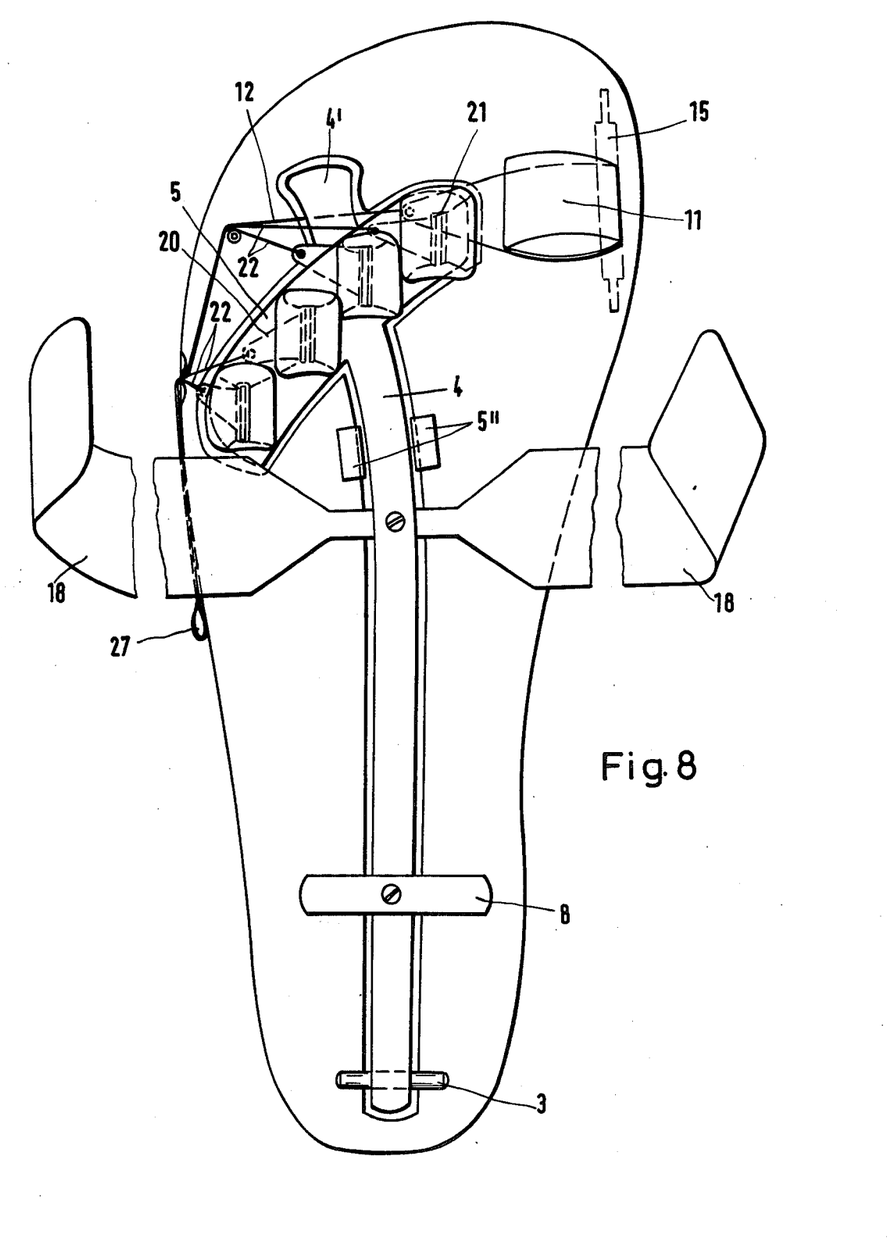

The embodiment of FIGS. 7 and 8 is similar to that seen in FIGS. 5 and 6 and, with regard to the lever arrangement, is similar to the example shown in FIGS. 1 to 4. Identical reference numerals have been used for similar structures. In this embodiment, the tongues 20 of secondary loops 19 penetrate the slots 21 of the secondary sole 6 downwardly, and penetrate further openings 26 of the activating cross-lever arm 5 which, in this embodiment, is placed further towards the front and is located below the toes. Also in this instance, the tongues 20 are wound up towards the side and obtain an initial stress from one each wire 22. This initial stress may be altered, by pulling tight and fastening the respective wire, for example slinging it around the studs 27. The initial stress may thereby be adjusted for each individual toe, including the initial stress of the loop 11 surrounding the large toe. The downwardly directed pressure of the activating cross-lever arm 5 immediately affects the secondary loops 19 and pulls the same downwards, resulting thereby in the hammer toe correction. Since the wire 12 of the large toe loop 11 is guided through below the frontal end 4' of the pressure lever arm, there results simultaneously also intermittently the Hallux Valgus correction. On the basis of attaching the splay foot bandage 18 to the activating cross-lever arm 5, there results simultaneously also the splay foot correction. For laterally securing the activating cross-lever arm 5, there may be provided, for example, a U-shaped guide element 5".

In all of the above described embodiments, unlike the devices of related U.S. Pat. Ser. No. 940,864, no holder means of the rear of the foot is provided. Thus, the foot in the mechanical release-phase of walking in the sandal is forced into an active movement, since it would have to hold the sandal which is coming loose from the foot. Otherwise the strength of this stress can thereby be arranged and precisely set by the adjustability of the initial stress of the splay foot bandage. This in and of itself known principle of the so-called foot exercising sandal, especially in connection with the instant invention, is of a special importance for increasing the local blood circulation and strength of the muscles of the foot.

Figure 9:
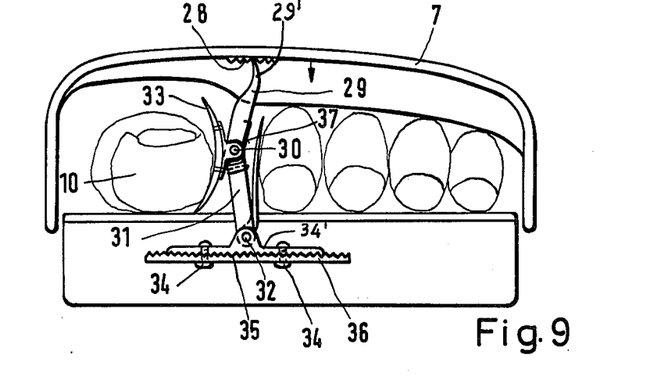
FIGS. 9 to 11 show in two front views and one top plan view a further embodiment of the Hallus Valgus correction.
Figure 10:
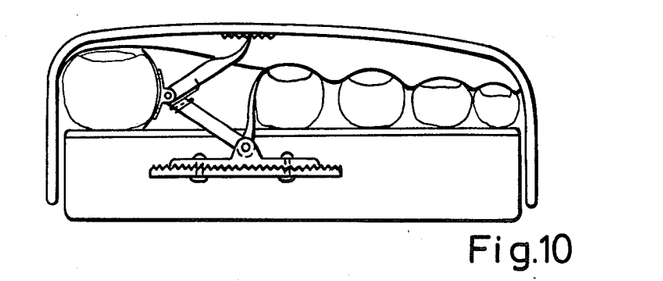
Figure 11:
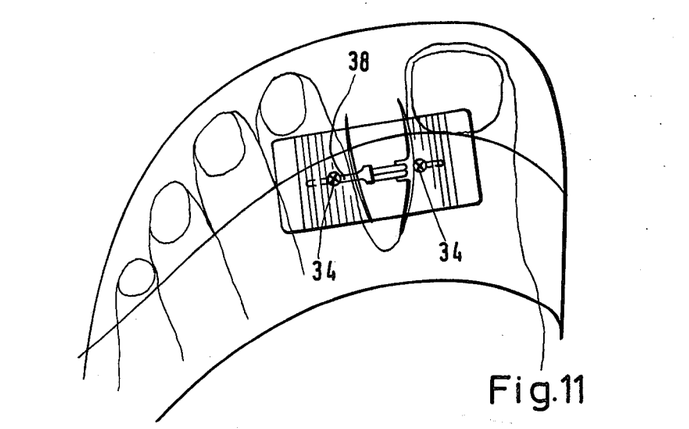

The embodiment of FIGS. 9 to 11 shows a Hallux Valgus correction by mechanical means on a toe-holding pressure bar 7 which may be activated according to the embodiment of FIGS. 1 to 4. It's bottom side is provided with a toothed portion or roughened surface 28 which can be engaged by the free end portion 29' of a lever arm 29 which is pivotably connected at pivot point 30 with a further lever arm 31. A pressure plate 33 is connected to this second lever arrangement 29, 31 at pivot point 30. The lever arm 31 is pivotably but fixedly connected to the sole by pivot 32. A downward pushing of bar 7 results in a movement of the pivot point 30 and the pressure plate 33 and via the same the large toe 10 moves to the medial. In order to adjust a basic or initial stress of this Hallux Valgus correction, screws 34 are released thus allowing a plate 34' carrying the pivot 32, to be adjusted with the help of a toothed portion 35 relative to a base plate 36 fixed to the sole 1 and may again be fixed in its new position by screws 34. A tension spring 37 normally retains the lever arrangement 29, 31 in the stretched position as seen in FIG. 9. FIG. 10 shows the stressed position of the Hallux Valgus correction. FIG. 11 shows the upper portion of the plate arrangement being displaceable toward the screws 34 by use of a slot-guide element 38.

Figure 12:
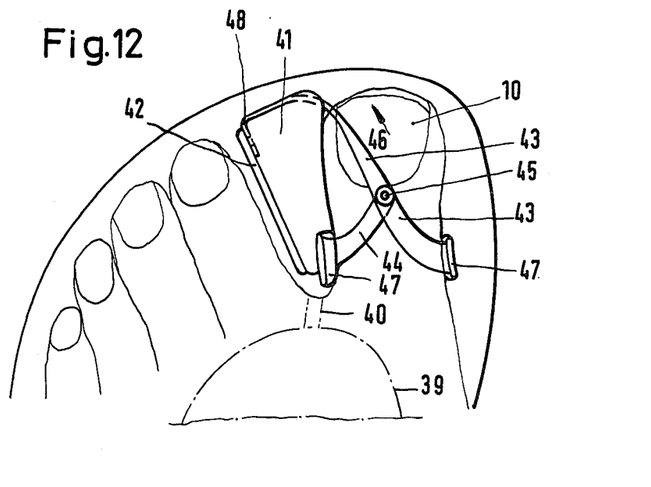
FIGS. 12 and 13 each show top plan views of the embodiment of a stretching of the large toe partially by way of mechanical and partially by hydraulical or pneumatic means, connected to a Hallus Valgus correction.
Figure 13:
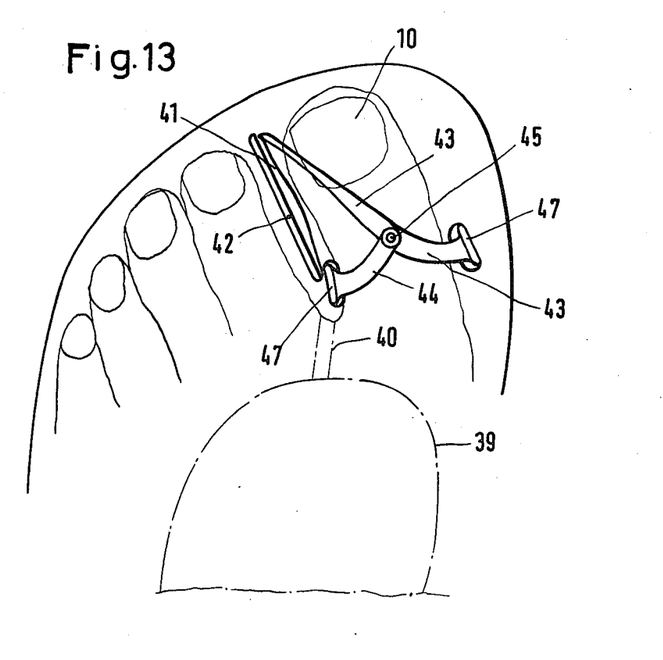

The embodiment of FIGS. 12 and 13 is a pneumatic or hydraulic, as well as mechanical device for the intermittent stretching of the large toe 10. In addition to a lever arrangement according to FIGS. 1 and 4, a hydraulic or pneumatic chamber 39 is positioned in the sole 1, which is only partially shown in the drawing. It is in communication with a toe chamber 41 via channel 40, with the chamber 41 resting on a toe-holding plate 42. A downward pressing of the foot compresses chamber 39, whereby the chamber 41 is expanded. This results in a movement of the large toe 10 to the medial. A first arm 43 which is made of a material which is bendable but resistant to longitudinal compression, for example, a synthetic material, is pivotally connected at 45 to a second arm 44 to form a clamp. The second arm 44 may be made of the same material. The arm 43 is guided around the chamber 41. With the expansion of the same, it is pulled into the direction of arrow 46 so that the two clamping shanks 47 grip the large toe 10 and pull it forward (see FIG. 12). FIG. 13 in contrast represents the relaxed position in which the chamber 39 is not compressed. The force of the pull may be altered in its basic value by means of an adjustable holder element 48 of arm 43 on the toe plate 42.

The identical pull effect could be obtained when the downward movement of activating lever arm 5 is translated mechanically on a pull- or pressure-device, which in a toothed grip holds the large toe (not illustrated).

Figure 14:
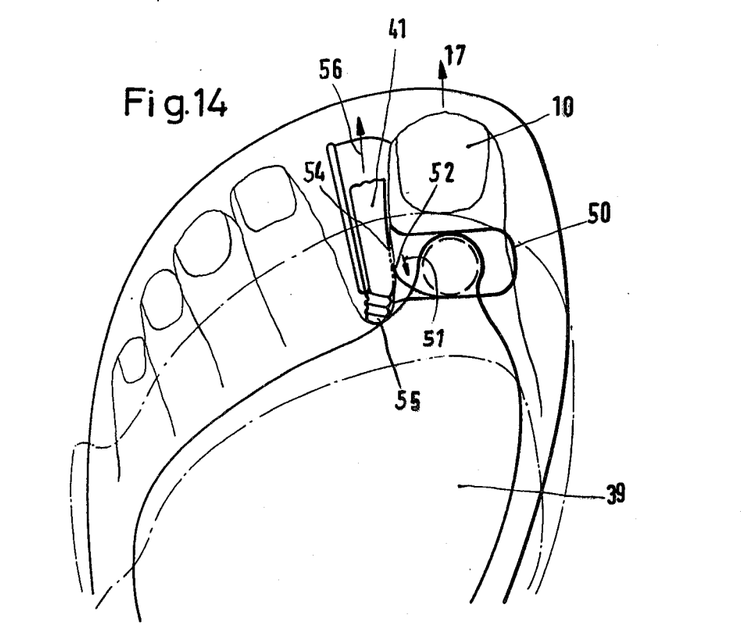
FIGS. 14 and 15 in a top plan view and in a lateral view (partially in cross-section) illustrate a purely pneumatically or hydraulically operating embodiment for stretching the large toe and for the Hallux Valgus correction.
Figure 15:
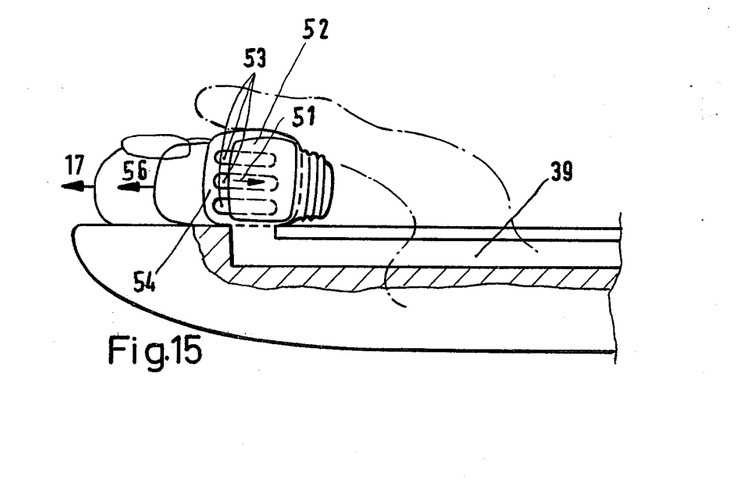

The embodiment of FIGS. 14, 15 shows finally a stretching of the large toe 10 by hydraulically or pneumatically operated means. A connecting means 40 leads from the sole chamber 39 to a ring 50 surrounding the large toe 10, and extending from there to the toe chamber 41 via a valve element, to be discussed in more detail. The valve consists of a resilient lid 52, which is movable along slit-shaped openings 53 of a separating wall 54 under the inside pressure of ring 50. The separating wall 54 is located between the inside of the ring 50 and the inside of the toe chamber 41. With increasing inside pressure in ring 50, the lid 52 releases the slots 53, i.e., gliding in the direction of arrow 56, and the toe chamber formed at one of its ends in the shape of a bellows 55 expands to the medial as well as in the direction of arrow 56. In the interim, the ring 50 has obtained such a high inside pressure and has expanded to the extent that it surrounds the toe 10, so that together with the movement of the toe chamber in the direction of arrow 56, the ring, and therewith the large toe 10, are moved in the direction of arrow 17. With this arrangement, a premature pull to ring 50 and therewith its gliding off from the large toe is prevented.

All discussed corrective measures are made intermittently. The characteristics shown by one embodiment may be altered accordingly, in connection with characteristics of other embodiments, or vice-versa.

It will now be seen that there is herein provided an orthopedic sandal which satisfies all of the objectives set forth above and others, including advantages of great practical utility and commercial importance.

The embodiments of the invention in which an exclusive property or privelige is claimed are defined as follows:

1. An orthopedic sandal for a foot comprising a sole having a rearward portion and a frontal portion, a lever arrangement connected to said sole for correcting the toes, the lever arrangement being located at least in the rearward portion of the sole and activated by means of a pressure on of the rearward portion of the sole.

2. The sandal according to claim 1, wherein means are provided for moving the large toe medially for correcting Hallux Valgus operatively associated with said lever arrangement.

3. The sandal according to claim 1 or 2, further comprising a splay foot bandage which surrounds the foot attached to the lever arrangement so that with each intermittent pressure of the foot the splay foot bandage presses the foot together.

4. The sandal according to claim 1 or 2, wherein said lever arrangement is movable in cavities of said sole, and is comprised of a cross-lever arm and a lever arm 1, connected to said cross-lever arm at a distance from a pivot point on the sole, whereby the cross-lever arm is positioned in said frontal portion of said sole for the correction of the respective parts of the foot.

5. The sandal according to claim 4, wherein the pivot point is positioned in the rearward portion of the sole.

6. The sandal according to claim 1, wherein a toe holding bar is positioned above the toes and attached to said arrangement and exers pressure on the toes two through five under activation.

7. The sandal according to claim 6, wherein said toe holding bar is adjustable upwardly and angularly.

8. The sandal according to claim 4, further comprising a secondary sole overlying said sole and having a flexible frontal portion and a rigid rearward portion, and a load distributing crossbar longitudinally adjustably mounted on said lever arm in the rearward portion of said sole.

9. The sandal according to claim 2, wherein said means for moving the large toe comprises a loop for encircling the large toe, and a pull wire associated therewith and said wire is guided in or around said sole, and is fastened thereon in an adjustable manner, and wherein said lever arrangement in their intermittent activation pull on said pull wire, providing same with a stress moving the large toe medially.

10. The sandal according to claim 9, further comprising secondary loops for encircling toes two to five and secondary pull wires, each connected to one secondary loop and having a free end, said secondary wires being guided in or around said sole and being fastened thereon by its free end in an adjustable manner and wherein said lever arrangement in their intermittent activation pull on said secondary wires providing same with a stress further supply corrective force for correcting hammertoe condition.

11. The sandal according to claim 10, wherein said pull wire and secondary pull wires are guided below said arrangement towards the loops.

12. The sandal according to claim 10, wherein said cross-lever arm is located directly below the secondary loops for gripping the toes two through five, and pulls the same immediately downwards during the intermittent operation.

13. The sandal according to claim 10, wherein the secondary loops for the gripping of the toes two through five are provided with tongues, which penetrate through slots of the secondary sole and with their protruding end portions, are laterally bended, whereby at these end portions are fastened the secondary pull wire.

14. The sandal according to claim 6, wherein said means for moving the large toe medially comprises a base plate mounted on said sole, and a second-lever arrangement, pivotally mounted on said base plate, said arrangement supports itself on the bottom side of the holding bar and carries a toe plate, whereby the arrangement is of such a fashion that a downward pressing of the holding bar via the second lever arrangement and toe plate effects a movement of the large toe medially.

15. The sandal according to claim 14, wherein the base plate comprises two sections, both sections being mutually adjustable in the direction of the Hallux Valgus correction and are fixable in the respective position.

16. The sandal according to claim 1 further comprising means for stretching the large toe coupled to the intermittent activation.

17. The sandal according to claim 16, wherein said means for stretching the large toe comprises the loop guided around a rotatably positioned and in the direction of the large toe moving roller so as to accept the rotation, and that the roller via a spiral threading, is positioned in the sole in such a manner so that it displaces itself during rotation in the longitudinal direction.

18. The sandal according to claim 16, further comprising a toothed holding device which grips the large toe and pulling the toe forwardly, being activated by means of the lowering movement of the foot.

19. The sandal according to claim 18, wherein the downwards movement of the lever arrangement is translated by a mechanical device into a pulling movement of the clamp-shaped holding device.

20. The sandal according to claim 18, wherein said toothed holder device comprises a toe chamber which is expandable by a fluid medium over which is guided a resilient pulling device which is thereby set in operation to pull the clamp-shaped holding device.

21. The sandal according to claim 16, wherein said means for stretching the large toe comprises a ring filled with a fluid medium and subjected to pressure surrounding the large toe and a hydraulic toe chamber in fluid connection therewith, said toe chamber when filled with the fluid medium moves the large toe medially as well as expands itself in the stretch-direction of the large toe, and thereby pulls the ring with it, whereby the large toe is stretched in longitudinal direction.

22. The sandal according to claim 21, wherein said fluid medium is guided from a compressible chamber, which is compressible by the pressure of the foot towards the ring, and for the entry of the medium into the toe chamber a valve means is provided between the toe chamber and the ring, which valve means opens with the increasing pressure inside the ring.

* * * * *